United States Patent
Ladet et al.

(10) Patent No.: US 10,441,678 B2
(45) Date of Patent: *Oct. 15, 2019

(54) IMPLANT FOR TISSUE REPAIR INCLUDING CHITOSAN

(71) Applicant: Sofradim Production, Trévoux (FR)

(72) Inventors: Sébastien Ladet, Caluire & Cuire (FR); Julien Claret, Villefranche-sur-Saône (FR)

(73) Assignee: Sofradim Production, Trevoux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/963,337

(22) Filed: Apr. 26, 2018

(65) Prior Publication Data

US 2018/0243472 A1  Aug. 30, 2018

Related U.S. Application Data

(60) Continuation of application No. 15/338,964, filed on Oct. 31, 2016, now Pat. No. 9,981,060, which is a (Continued)

(51) Int. Cl.
| | |
|---|---|
| *A61L 27/20* | (2006.01) |
| *A61K 9/00* | (2006.01) |
| *A61K 47/36* | (2006.01) |
| *A61L 27/56* | (2006.01) |
| *A61K 45/00* | (2006.01) |

(Continued)

(52) U.S. Cl.
CPC ............ *A61L 27/20* (2013.01); *A61K 9/0024* (2013.01); *A61K 45/00* (2013.01); *A61K 47/36* (2013.01); *A61L 27/24* (2013.01); *A61L 27/48* (2013.01); *A61L 27/54* (2013.01); *A61L 27/56* (2013.01); *A61L 27/58* (2013.01); *B05D 5/00* (2013.01); *B32B 37/24* (2013.01); *A61L 2300/604* (2013.01); *A61L 2430/00* (2013.01); *Y10T 29/49947* (2015.01); *Y10T 156/10* (2015.01)

(58) Field of Classification Search
CPC .......... A61L 27/20; A61L 27/24; A61L 27/54; A61L 27/56; A61L 27/58; A61L 2430/00; A61K 9/0024; A61K 47/36
See application file for complete search history.

(56) References Cited

U.S. PATENT DOCUMENTS

| | | |
|---|---|---|
| 6,596,304 B1 | 7/2003 | Bayon et al. |
| 8,968,762 B2 | 3/2015 | Ladet et al. |

(Continued)

FOREIGN PATENT DOCUMENTS

| | | | |
|---|---|---|---|
| WO | 2007111416 | * | 10/2007 |
| WO | 2007111416 A1 | | 10/2007 |

(Continued)

OTHER PUBLICATIONS

Baxter, et al., Molecular Weight and Degree of Acetylation of High-Intensity Ultrasonicated Chitosan, Food Hydrocolloids, 19 (2005) 821-830.

(Continued)

*Primary Examiner* — Carlos A Azpuru

(57) ABSTRACT

Mono- and multi-layered implants include at least one porous layer made from a freeze dried aqueous solution containing chitosan, the solution having a pH of less than about 5.

24 Claims, 14 Drawing Sheets

Related U.S. Application Data division of application No. 14/621,519, filed on Feb. 13, 2015, now Pat. No. 9,480,774, which is a continuation of application No. 13/637,440, filed as application No. PCT/IB2011/001213 on Mar. 28, 2011, now Pat. No. 8,968,762.

(60) Provisional application No. 61/317,881, filed on Mar. 26, 2010.

(51) Int. Cl.
  *B05D 5/00* (2006.01)
  *B32B 37/24* (2006.01)
  *A61L 27/24* (2006.01)
  *A61L 27/48* (2006.01)
  *A61L 27/54* (2006.01)
  *A61L 27/58* (2006.01)

(56) References Cited

U.S. PATENT DOCUMENTS 9,480,774 B2  11/2016  Ladet et al.
9,981,060 B2  5/2018  Ladet et al.

FOREIGN PATENT DOCUMENTS

| WO | 2009027537 | * | 3/2009 |
| WO | 2009027537 A1 | | 3/2009 |
| WO | 2009031047 | * | 3/2009 |
| WO | 2009031047 A2 | | 3/2009 |

OTHER PUBLICATIONS

Ruiz-Caro et. al., Characterization and Dissolution Study of Chitosan Freeze-Dried Systems for Drug Controlled Release, Molecules 2009, 14, 4370-4386.

International Search Report corresponding to International Application No. PCT/IB2011/001213, completed on Oct. 7, 2011, dated Oct. 14, 2011; 2 pages.

Le Devedec et al., Separation of Chitosan Oligomers by Immobilized Metal Affinity Chromatography, Journal of Chromatography A, Jun. 20, 2008; 1194(2), pp. 165-171.

Tomihata et al., In vitro and in vivo degradation of films of chitin and its deacetylated derivatives, Biomaterials, vol. 18, No. 7, pp. 567-575, 1997.

Kim et al., Enzymatic production and biological activities of chitosan oligosaccharides (COS): a review, Carbohydrate Polymers, vol. 62, No. 4, pp. 357-368, 2005.

Kurita, et al., "Enzymatic degradation of .beta.-chitin: susceptibility and the influence of deacetylation" Carbohydrate Polymers, vol. 42, pp. 19-21 (2000).

* cited by examiner

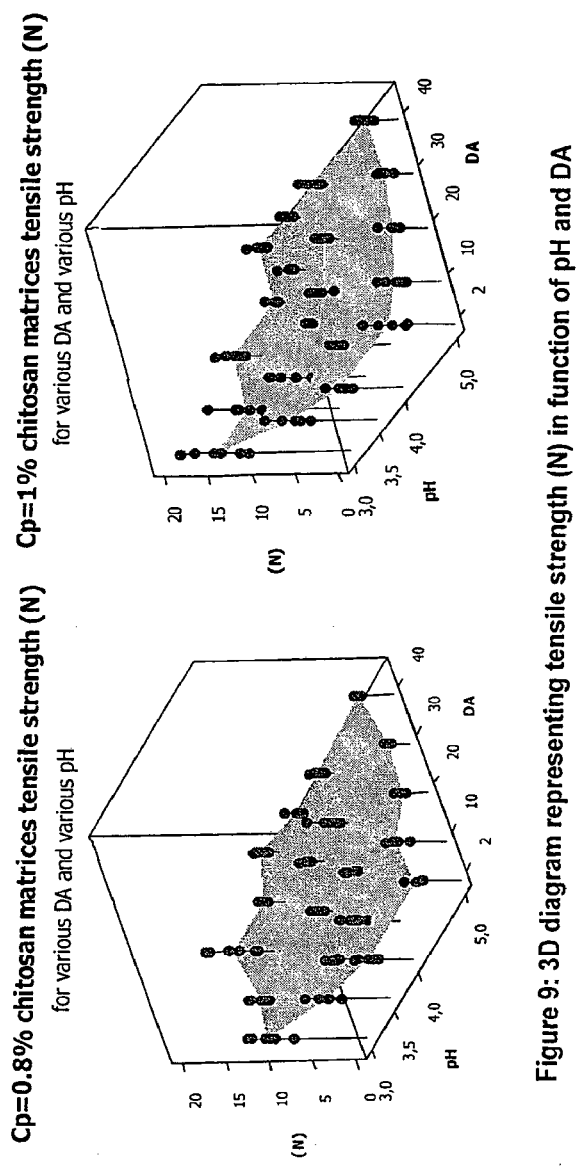
Figure 9: 3D diagram representing tensile strength (N) in function of pH and DA

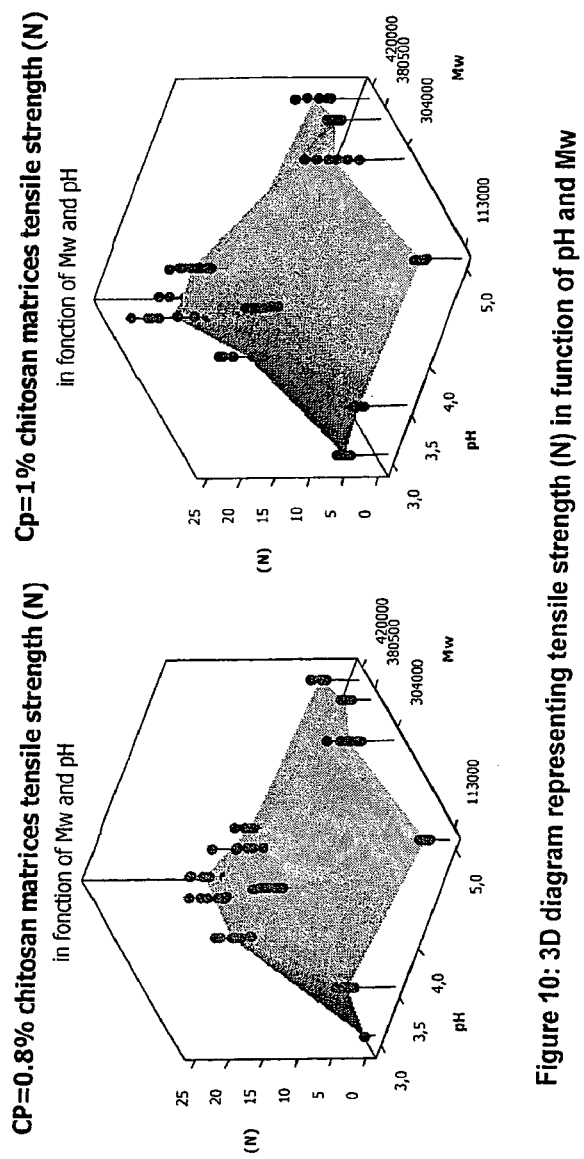
Figure 10: 3D diagram representing tensile strength (N) in function of pH and Mw

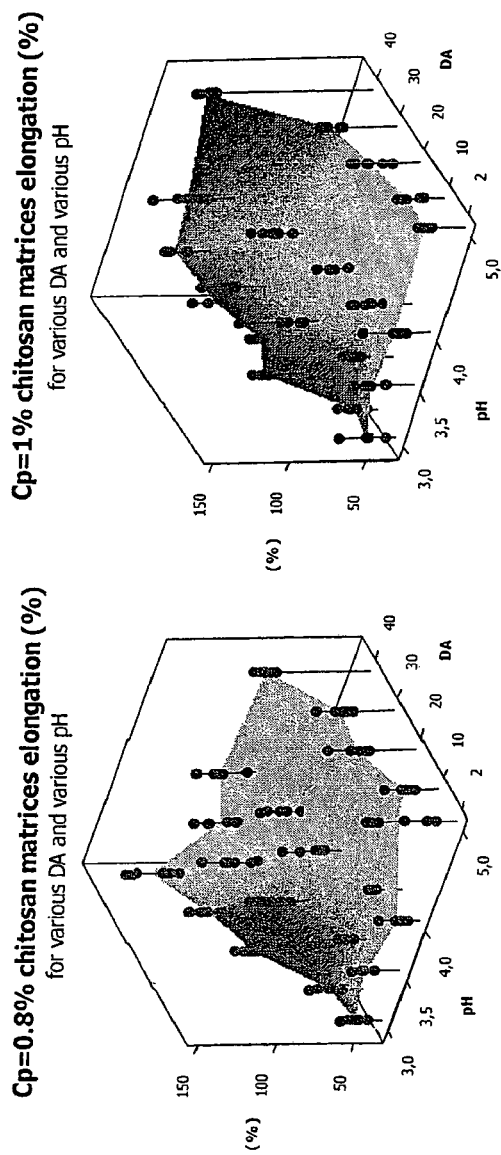
Figure 11: 3D diagram representing elongation (%) in function of pH and DA

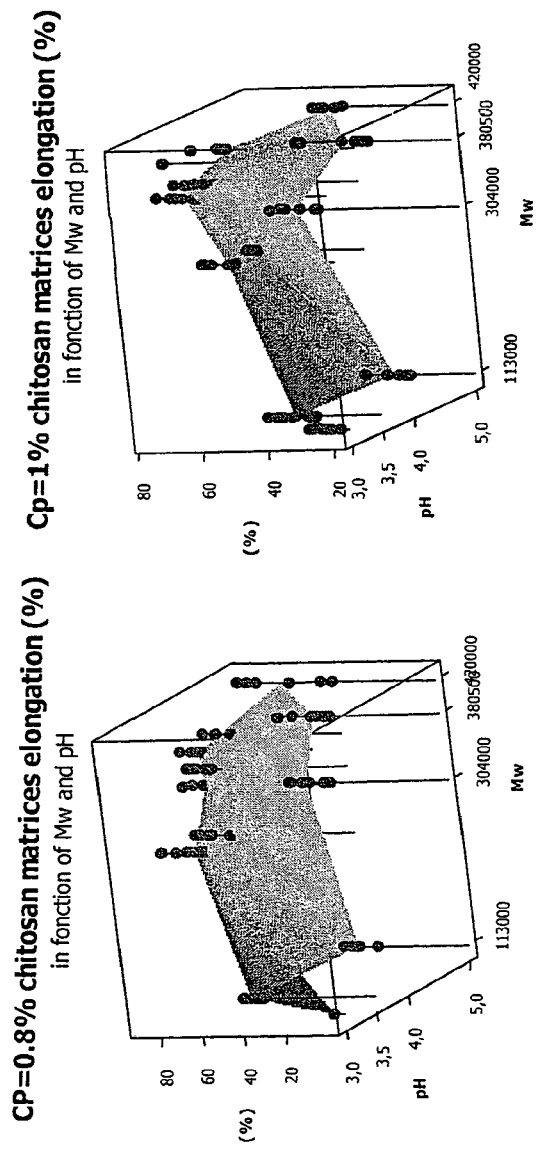
Figure 12: 3D diagram representing elongation (%) in function of pH and Mw

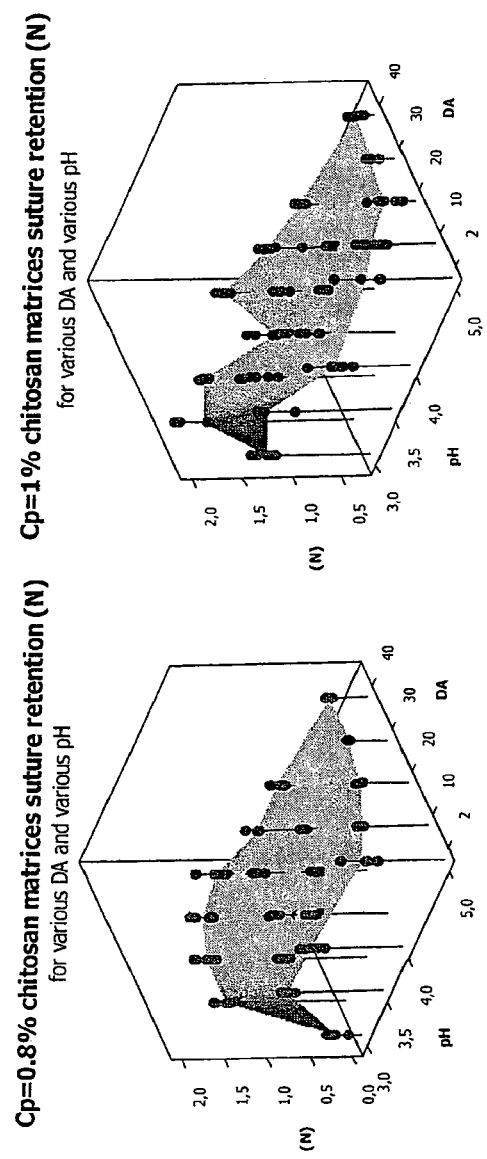
Figure 13: 3D diagram representing suture retention (N) in function of pH and DA

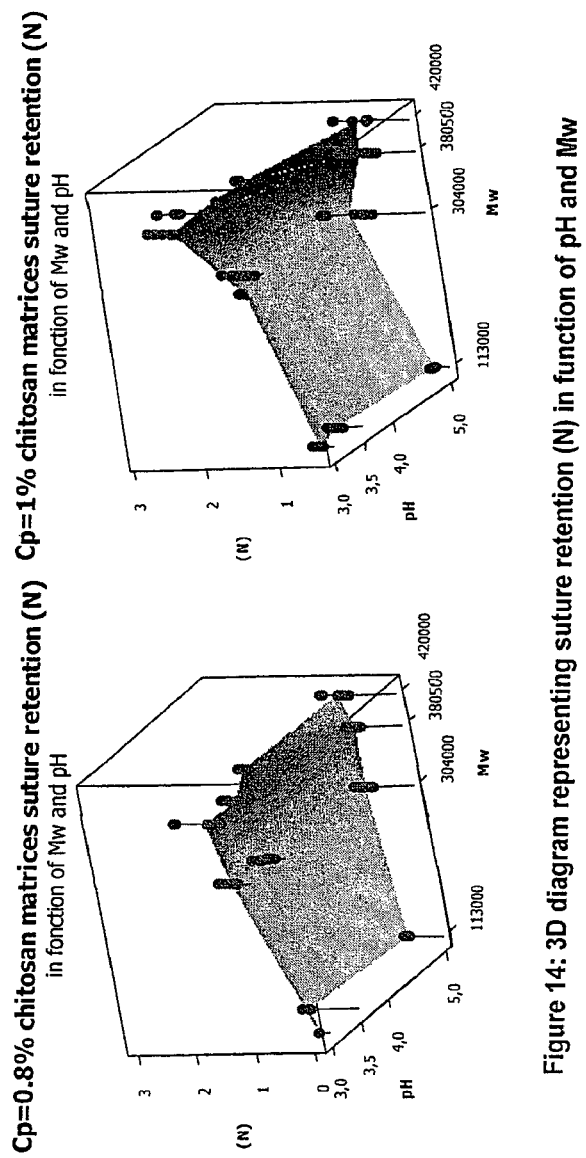
Figure 14: 3D diagram representing suture retention (N) in function of pH and Mw

IMPLANT FOR TISSUE REPAIR INCLUDING CHITOSAN

CROSS-REFERENCE TO RELATED APPLICATIONS

This application is a continuation of U.S. patent application Ser. No. 15/338,964 filed Oct. 31, 2016, which is a divisional of U.S. patent application Ser. No. 14/621,519 filed Feb. 13, 2015, now U.S. Pat. No. 9,480,774, which is a continuation of U.S. patent application Ser. No. 13/637,440 filed Dec. 4, 2012, now U.S. Pat. No. 8,968,762, which is a National Stage Application of PCT/IB2011/001213 filed Mar. 28, 2011, which claims benefit of U.S. Provisional Application No. 61/317,881 filed Mar. 26, 2010, and the disclosures of each of the above-identified applications are hereby incorporated by reference in their entirety.

TECHNICAL FIELD

The present disclosure relates to implants, more particularly mono- or multi-layer implants which include at least one porous chitosan-containing layer made from an aqueous solution of one or more chitosans, wherein the aqueous solution is freeze-dried at a pH of less than about 5.

BACKGROUND

Repairing damaged meningeal membranes has largely focused on implants (known as dural substitutes) which are grafted over damaged dura mater and are designed to replace and/or regenerate the damaged tissue. Current dural substitutes based on collagen matrices provide a good bioresorbable and safe substitute, compared to xenograft or allograft implants. Nevertheless, dural substitutes based on collagen matrices may display inferior mechanical properties such as short persistence, inferior tensile strength and low suture retention for use in infratentorial or spine areas. Synthetic dural substitutes may show improved mechanical and watertight properties, but generally are not absorbable, show a lack of conformability and are less easy to use.

The present disclosure relates to biocompatible and bioresorbable chitosan based implants having enhanced mechanical properties including increased suture anchoring strength and increased tensile strength. These enhanced mechanical properties may be achieved by controlling the pH during processing of the implant and may eliminate the need for a chemical cross-linking agent. The present matrices may be used in a variety of medical applications, including, for example surgical implants.

SUMMARY

Implantable structures in accordance with the present disclosure include a porous chitosan-containing layer that serves as an implant to support tissue repair and/or tissue regeneration while providing suture retention and a controlled and desirable time of in vivo absorption. The porous chitosan-containing layer is made from an aqueous solution of one or more chitosans. Control of the pH of the solution after the solubilization of the chitosan induces changes in the solution, which may impact the mechanical properties of the final implant. The type of chitosan used to make the porous layer may provide a desired in vivo persistence profile. The present implants may be used as a substitute for and/or as a scaffold to regenerate tissue, such as, for example dura mater, liver, lung, bowel, and the like.

An aspect of the invention is an implant comprising a freeze-dried porous layer derived from an aqueous solution containing chitosan, the aqueous solution having a pH of less than about 5. The aqueous solution containing chitosan may comprise chitosan having a degree of acetylation ranging from about 0 to about 60%. The aqueous solution containing chitosan may comprise chitosan in an amount from about 0.1 to about 10% of the solution by weight. In embodiments, the aqueous solution containing chitosan comprises chitosan in an amount from about 0.8 to about 5% of the solution by weight.

In embodiments, the pH of the aqueous solution containing chitosan is from about 2.5 to about 4.0, preferably from about 3.0 to about 3.5. Implants made from an aqueous solution containing chitosan at such pH show in particular good tensile strength and good suture retention. In embodiments, the chitosan may have a degree of acetylation of less than 30%, preferably less than 20%. In particular, the chitosan porous layer of the implant of the invention shows good tensile strength when the pH of the chitosan solution is less than 4, preferably between 3 and 3.5, and when the degree of acetylation of the chitosan is less than 30%, preferably less than 20%.

In embodiments, the chitosan has a molecular weight equal to or greater than 304000 g/mol. In particular, the chitosan porous layer of the implant of the invention shows good tensile strength and good suture retention when the pH of the chitosan solution is less than 4, preferably between 3 and 3.5, and when the molecular weight of the chitosan is equal or greater than 304000 g/mol.

In embodiments, the chitosan has a degree of acetylation equal to or greater than 10%, preferably equal to or greater than 20%.

In embodiments, the aqueous solution containing chitosan comprises chitosan in an amount from about 0.8 to 1% of the solution by weight, preferably in an amount of 1% of the solution by weight. In particular, the chitosan porous layer of the implant of the invention shows good elongation when the degree of acetylation of the chitosan is equal or greater than 10%, preferably equal or greater than 20%, especially when the concentration of the chitosan in the chitosan solution is 1% by weight.

In embodiments, the aqueous solution further comprises glycerine.

In embodiments, the aqueous solution comprises a plurality of chitosan polymers with different degrees of acetylation.

In embodiments, the porous layer further comprises at least one bioactive agent.

In embodiments, the freeze-dried porous layer has a tensile strength of at least about 4N. In embodiments, the freeze-dried porous layer has an elongation percentage of at least about 40%, preferably of at least about 60%. In embodiments, the freeze-dried porous layer has a suture anchoring strength of at least about 0.8N. In embodiments, the freeze-dried porous layer has a thickness of about 0.1 mm to about 10 mm in a dried state.

In embodiments, the implant further comprises a non-porous layer. The non-porous layer may comprise a collagen containing film. The collagen film may comprise a collagen selected from the group consisting of non-heated oxidized collagen, heated oxidized collagen, non-oxidized heated collagen and combinations thereof. The collagen film may further comprise at least one macromolecular hydrophilic additive. The at least one macromolecular additive may be selected from the group consisting of polyalkylene glycols, polysaccharides, oxidized polysaccharides, mucopolysaccharides, glycerin and combinations thereof.

The non-porous layer may have a thickness of less than about 100 µm in a dry state.

Another aspect of the invention is a method of forming an implant comprising:

pouring an aqueous solution containing chitosan having a pH of less than about 5 onto a substrate; and forming a porous layer by freeze-drying the aqueous solution.

Pouring the aqueous solution containing chitosan may comprise pouring an aqueous solution containing chitosan, water and at least one acid. Pouring the aqueous solution containing chitosan may comprise pouring an aqueous solution containing chitosan, water and at least one acid and a bioactive agent. Pouring the aqueous solution containing chitosan may comprise pouring an aqueous solution having a pH of from about 3 to about 3.5. Pouring the aqueous solution containing chitosan may comprise pouring an aqueous solution comprising about 1.0% chitosan by weight of the solution.

In embodiments, the method further comprises rinsing the porous layer with a composition containing at least one alkaline agent. Rinsing the porous layer with a composition containing at least one alkaline agent may comprise rinsing the porous layer with a composition containing an alkaline agent selected from the group consisting of sodium hydroxide, calcium hydroxide, aluminium hydroxide, potassium hydroxide, sodium phosphate, sodium carbonate, ammonia and combinations thereof.

In embodiments, the method may further comprise washing the rinsed porous layer. The method may further comprise freeze-drying the washed porous layer.

In embodiments, the method may further comprise at least partially gelling a solution containing collagen; and applying the porous layer onto the at least partially gelled collagen solution.

In embodiments, the method comprises attaching the porous layer to a non-porous film comprising collagen. Attaching the porous layer to a non-porous film may comprise adhering the porous layer to the non-porous film using chemical bonding, photoinitiation, surgical adhesives, surgical sealants, surgical glues or combinations thereof. Alternatively, attaching the porous layer to a non-porous film may comprise securing the porous layer to the non-porous film using mechanical means selected from the group consisting of pins, rods, screws, staples, clips, sutures, and combinations thereof.

BRIEF DESCRIPTION OF THE DRAWINGS

The foregoing objects and advantages of the disclosure will become more apparent from the reading of the following description in connection with the accompanying drawings, in which:

FIG. 9 shows 3D diagrams representing the tensile strength (N) in function of pH and DA for freeze-dried porous layers of implants of the invention for a concentration in chitosan of 0.8%, respectively 1%;

FIG. 10 shows 3D diagrams representing the tensile strength (N) in function of pH and Mw for freeze-dried porous layers of implants of the invention for a concentration in chitosan of 0.8%, respectively 1%;

FIG. 11 shows 3D diagrams representing elongation (%) in function of pH and DA for freeze-dried porous layers of implants of the invention for a concentration in chitosan of 0.8%, respectively 1%;

FIG. 12 shows 3D diagrams representing elongation (%) in function of pH and Mw for freeze-dried porous layers of implants of the invention for a concentration in chitosan of 0.8%, respectively 1%;

FIG. 13 shows 3D diagrams representing suture retention (N) in function of pH and DA for freeze-dried porous layers of implants of the invention for a concentration in chitosan of 0.8%, respectively 1%;

FIG. 14 shows 3D diagrams representing suture retention (N) in function of pH and Mw for freeze-dried porous layers of implants of the invention for a concentration in chitosan of 0.8%, respectively 1%;

DETAILED DESCRIPTION

Figure 1:
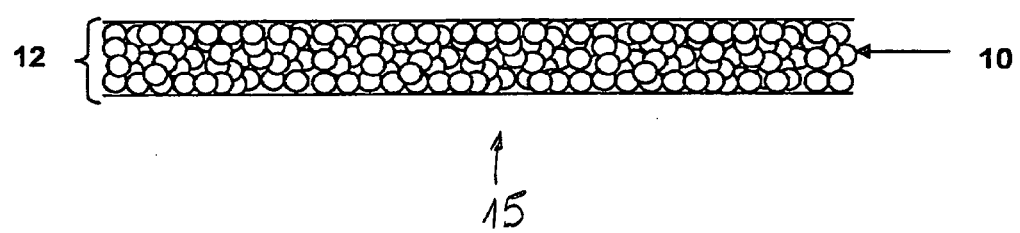
FIG. 1 is an illustration of a single-layer implant of porous chitosan in accordance with an embodiment of the present disclosure.

The present disclosure relates to implants for use in medical applications, such as, for example, an implant or scaffold for biological tissue repair and/or biological tissue regeneration. The implant may be used in any procedure involving for example, repair or substitution of biological tissue. In embodiments, the implant may be used for the repair or substitution of dura mater.

The implant may be composed of one or more layers. At least one of the layers may be a porous layer that functions, for example, as a tissue support during tissue regeneration. The method of forming implants described herein may provide enhanced mechanical properties, such as, for example, better suture retention strength, than matrices formed from purified natural polymers, even when the natural polymer implant is cross-linked with chemical agents, such as formaldehydes or glutaraldehyde. These enhanced mechanical properties may be achieved by controlling the pH during processing of the implant and may eliminate the need for a chemical cross-linking agent. Moreover, the suture retention strength may be modulated by varying the concentration of chitosan used in the formulation. Although described herein with reference to a matrix, mesh, or scaffold, the implant may be any type of implant suitable for allowing tissue integration.

The enhanced mechanical properties possessed by the implants in accordance with the present disclosure may include a tensile strength of about 4 N (Newtons) or greater, an elongation percentage of about 60% or greater, and/or a suture anchoring strength of about 0.8 N or greater. In embodiments, the tensile strength may be from about 4 N to about 20 N, in embodiments from 10 N to about 18 N. In embodiments, the elongation percentage may be from about 60% to about 85%, in embodiments from about 70% to about 80%. In embodiments, the suture anchoring strength may be from about 0.8 N to about 1.5 N.

As stated above, the enhanced mechanical properties of the implants described herein may be due to the process used during the formation of the implant. During processing, an aqueous solution of chitosan is used to form a porous layer of the implant. Chitosan solubilised in water may have a pH of approximately 5. It is envisioned that the chitosan may be solubilised in any water suitable for implantation including sterile water, deionized water, distilled water, and the like.

In accordance with the present disclosure, the pH of the solubilized chitosan may be decreased by adding a certain amount of at least one acid until the solution has a pH under a value of about 4 in water. It is believed that control of the pH after solubilization of the chitosan induces a specific interaction of the chitosan polymers in solution, thereby impacting the mechanical properties of the resulting implant.

In embodiments, the implant may include more than one layer. In embodiments, at least one of the layers is a porous chitosan-containing layer. The layers may be bioabsorbable and may be porous or non-porous. The bioabsorbable implants may include one or more layers which are non-porous. In embodiments, the multilayer implants may also include a reinforcement layer which includes a mesh or fiber which may stiffen the porous implant. The layers of the implants described herein may be formed from the same or different biocompatible materials; at least one of the materials may be a chitosan polymer. In embodiments, the implant may include two or more layers, such as an implant which includes a porous chitosan layer and a non-porous collagen layer.

Chitosan, Glycosaminoglycans and Derivatives of these

Chitosan is a natural polysaccharide derived from the chitin. Chitin may be extracted from a natural source, for example, animal tissue such as squid pens and shrimp shells, vegetable sources such as mushrooms (e.g., "champignon de paris"), or chitin may be synthesized by modified microorganisms such as bacteria, or the chitin may be synthetically produced. Derivatives of chitosan include, for example partially and/or fully deacetylated chitosan. The chitosan may have a degree of acetylation (DA) of about 0% to about 60%. In embodiments, the chitosan may have a degree of acetylation (DA) of about 1% to about 40%. Chitosan having different degrees of acetylation may be produced by a heterogeneous deacetylation process or by a homogenous reacetylating process from fully deacetylated glycosaminoglycans.

The term "glycosaminoglycan" as used herein may include complex polysaccharides having repeating units of either the same saccharide subunit or two or more different saccharide subunits. Glycosaminoglycans may include, for example, dermatan surfate, hyaluronic acid, chondroitin sulfates, chitin, heparin, keratan sulfate, keratosulfate, and derivatives thereof. Chitosan derivatives may include partially and fully deacetylated versions of these glycosaminoglycan compounds, such as, deacetylated hyaluronic acid. Except in the working examples or unless otherwise indicated, as used herein the term, "chitosan" includes glycosaminoglycans, chitosan, and chitosan derivatives.

In embodiments, the chitosan has a molecular weight ranging from about 100 to about 3,000,000 g/mol. In some embodiments, the chitosan has a molecular weight ranging from about 179 (chitosan monomer) to about 1,000,000 g/mol. In embodiments, the chitosan also displays a low polydisperity index between about 1 to about 2. In embodiments, the chitosan may be a mixture of chitosans having different degrees of acetylation. The in vivo persistence of the implant may vary depending on the degree of acetylation of the chitosan or glycosaminoglycan used to form the porous layer of the implant.

Porous Layer

The implants described herein include at least one porous layer made from an aqueous solution of chitosan, wherein the chitosan solution is freeze-dried at a pH of less than about 5. In embodiments, the porous chitosan layer is formed by solubilizing chitosan in deionized water with a stoichiometric amount of acid and a chitosan polymer concentration ranging from about 0.1% to about 10% (w/w). The solubilised chitosan displays a pH less than about 5 and may be freeze-dried to form a porous layer. In embodiments, the pH of the aqueous chitosan solution may be adjusted downward to a pH less than about 4 prior to drying. In embodiments, the chitosan polymer concentration may be from about 0.8% to about 5.0%, in embodiments, about 1.0%.

Table 1 shows illustrative embodiments of polymer solutions suitable for use in forming the porous chitosan layer using a freeze-drying process.

TABLE 1

| Batch No. | Polymer concentration in solution (w/w) | pH solution before freeze drying |
|---|---|---|
| A | 1.00% | 5.083 |
| B | 0.80% | 5.101 |
| C | 1.00% | 3.465 |
| D | 0.80% | 3.495 |
| E | 1.00% | 3.011 |
| F | 0.80% | 3.002 |
| G | 0.80% | 0.960 |

In accordance with the present disclosure, the pH of the aqueous chitosan solution may be adjusted to a value of less than about 5. In order to obtain implants which display one or more enhanced mechanical properties as described herein, the pH of the aqueous chitosan solution may be specifically adjusted to a value between about 2.5 and about 4.0. In embodiments the pH of the chitosan solution may adjusted to a value between about 3.0 and about 3.5.

Any pH adjusting agent, in concentrated or dilute form, may be added to the chitosan solution to adjust the pH of the solution. Agents for adjusting pH may include acids. Some non-limiting examples acids include, sulphuric acid, acetic acid, phosphoric acid, hydrochloric acid, nitric acid, formic acid, oxalic acid, citric acid, malic acid, maleic acid, adipic acid, pyruvic acid, tartaric acid and combinations thereof. Alkalizing agents may also be used to adjust the pH and some non-limiting examples include, hydroxides such as ammonium hydroxide, sodium hydroxide, potassium hydroxide and other bases such as sodium carbonate, ammonia, and sodium acetate. In embodiments, the agent for adjusting the pH of the chitosan solution may be acetic acid.

The pH adjusted solution may then freeze-dried to form a chitosan porous layer which exhibits enhanced mechanical properties. Any suitable method known to those skilled in the art of freeze-drying may be used to transform the pH adjusted chitosan solution into a porous implant. In embodiments, the pH adjusted aqueous solution of chitosan may be poured into an inert support, such as, for example, a flat tray made from a hydrophobic material such as PVC or polystyrene. The support containing the chitosan solution may then be freeze-dried to form a porous layer. The resulting porous chitosan layer may exhibit enhanced mechanical properties.

Optionally, glycerine may be added to the aqueous chitosan solution used to form the porous chitosan layer. When present, the concentration of glycerine in the solution may be from about 2 to about 10 times less than that of the chitosan. In embodiments, the concentration of glycerine in the solution may be less than about one-third of the amount of chitosan.

In embodiments, the porous chitosan layer may be composed of a plurality of different chitosan monomers or polymers, wherein each of the chitosan monomers or polymers has a different degrees of acetylation (DA). Chitosan has a degradation time related to its degree of acetylation (Kurita et al., Carbohydrate Polymers, Vol. 42 pp. 19-21, 2000; Tomihata et al., Biomaterials, Vol. 18 no. 7 pp. 567-575, 1997). A combination of chitosan monomers or polymers with different degrees of acetylation may produce a porous chitosan layer having a combination of slow and fast biodegrading chitosan. In embodiments, such a combination may be advantageous, for example, for progressive cell colonization of the porous layer. This allows the preparation of various matrices having an adjustable in-vivo degradation profile. In embodiments, the porous chitosan layer persists at the site of implantation at least two weeks before being fully absorbed.

In embodiments, molecules released from the controlled degradation of the porous chitosan layer, may advantageously confer to the implant biological activities, such as, for example, antimicrobial, anticancer, antioxidant, and immunostimulant effects (Kim et al., Carbohydrate Polymers, Vol. 62, Issue 4, pp. 357-368, 2005) and may provide both biocompatibility and biodegradability, bioactive properties to the implant. The biological properties of released chitosan oligopolymers may also enhance tissue regeneration and extend the use of the implant, for example, to surgical sites with a high risk of contamination. In embodiments, the degradation of a slowly biodegrading oxidized collagen layer and a chitosan layer having a high DA, e.g., 35≤DA≤60, in vitro in the presence of viable cells and in vivo, helps to increase the interconnected porosity assisting in the regeneration of healthy tissue.

The porous chitosan layer may have a thickness of about 0.1 mm to about 10 mm in a dried state. In multi-layer embodiments, the porous layer may be from about 0.2 mm to about 5 mm thick in a dried state. The porous layer displaying such a thickness may have a density of from about 0.1 mg of polymer per square centimeter (length× width of the porous layer) to about 50 mg of polymer per square centimeter. In embodiments the density of the porous layer may range from about 0.25 mg of polymer per square centimeter to about 20 mg of polymer per square centimeter.

The size of the pores in such a porous layer can be from about 10 μm to about 1000 μm, in embodiments from about 50 μm to about 500 μm. The porous layer may be optionally compacted by using a press or any other appropriate means, so as to obtain a thickness comprised between 0.1 mm and 5 mm, and in some embodiments between about 0.1 mm and about 3 mm.

Non-Porous Layer Formation

In some embodiments, the implants described herein may be multi-layered. The additional layers may be porous or non-porous layers of biocompatible materials. In embodiments, the multi-layered implant may include a porous layer as described herein and a non-porous layer attached thereto. The non-porous layer may be, for example, a biodegradable film. The biodegradable film may be made from any biocompatible material suitable for implantation. The biocompatible material may be bioabsorbable. In embodiments, a non-porous layer may prevent the implant from adhering to the surrounding tissue and minimize the leakage of any physiological fluid.

In embodiments, the non-porous layer may include collagen and/or collagen derivatives. In embodiments, the collagen films may further include a macromolecular compound, such as, for example, polyethylene, glycerol and combinations thereof. Suitable collagen films may be made from non-heated oxidized collagen, heated oxidized collagen, non-oxidized heated collagen or combinations thereof. In embodiments, the collagen film may be made from heated oxidized collagen, as described in U.S. Pat. No. 6,596,304, the entire disclosure of which is incorporated herein by reference.

Table 2 gives illustrative concentrations of collagen solutions useful in forming a non-porous layer.

TABLE 2

| Non heated oxidized collagen content | 0.1%-3% (w/w) |
|---|---|
| Heated Oxidized collagen content | 0.1%-6% (w/w) |
| Heated collagen content | 0.1%-6% (w/w) |

In embodiments, at least one macromolecular hydrophilic additive that is chemically unreactive with the collagen may be added to the solution used to form the non-porous layer. "Chemically unreactive with the collagen" as used herein means a hydrophilic compound which is not likely to form covalent bonds with collagen.

The macromolecular hydrophilic additive advantageously may have a molecular weight in excess of 3,000 Daltons, in embodiments from about 3,000 to about 20,000 Daltons. Illustrative examples of suitable macromolecular hydrophilic additives include polyalkylene glycols (such as polyethylene glycol), polysaccharides (e.g., starch, dextran and/or cellulose), oxidized polysaccharides, and mucopolysaccharides. It should of course be understood that combinations of macromolecular hydrophilic additives may be used. The concentration of hydrophilic additive(s) may typically be from about 2 to about 10 times less than that of the collagen.

Following implantation, the macromolecular hydrophilic additive may be eliminated by diffusion through the non-porous layer, in a few days. The swelling of the macromolecular hydrophilic additive may advantageously promote degradation of a collagenic non-porous layer in less than about one month in situ.

In embodiments, glycerine may be combined with the collagen to form the non-porous layer. When present, the concentration of glycerine in the solution may be from about 2 to about 10 times less than the concentration of collagen.

In embodiments, the concentration of glycerine in the solution may be less than about one-third of the collagen concentration.

In embodiments, solutions used to form the non-porous layer include, for example, from about 0.1 to about 3% w/w of non-heated oxidized collagen, up to 2% w/w polyethylene glycol and up to 1% w/w glycerol. In the dry state, the resulting non-porous layer may contain from about 40 to about 100% w/w of non-heated oxidized collagen, up to 60% w/w polyethylene glycol and up to 20% w/w glycerol.

In embodiments, solutions for forming the non-porous layer may include from about 0.5 to about 1.5% w/w of non-heated oxidized collagen, from about 0.6 to about 0.9% w/w polyethylene glycol and from about 0.3 to about 0.6% w/w glycerol. In the dry state, the resulting non-porous layer may contain from about 60 to about 90% w/w of non-heated oxidized collagen, from about 15 to about 30% w/w polyethylene glycol and from about 5 to about 15% w/w glycerol.

Other examples of solutions useful in forming the non-porous layer include from about 0.1 to about 3% w/w of heated oxidized collagen, from about 0.1 to about 3% w/w of heated collagen, up to 2% w/w polyethylene glycol and up to 1% w/w glycerol. In the dry state, the resulting non-porous layer may contain from about 40 to about 100% w/w of heated oxidized collagen, about 40 to about 100% w/w of heated collagen, up to 60% w/w polyethylene glycol and up to 20% w/w glycerol.

In embodiments, solutions useful in forming the non-porous layer include from about 0.5 to about 1.5% w/w of non-heated oxidized collagen, from about 0.5 to about 1.5% w/w of heated collagen, from about 0.6 to about 0.9% w/w polyethylene glycol and from about 0.3 to about 0.6% w/w glycerol. In the dry state, the resulting non-porous layer may contain from about 60 to about 90% w/w of heated oxidized collagen, from about 60 to about 90% w/w of heated collagen, from about 15 to about 30% w/w polyethylene glycol and from about 5 to about 15% w/w glycerol.

The thickness of the non-porous layer may be less than about 100 µm thick, and in embodiments may range from about 15 µm to about 75 µm thick in a dry state.

Any bioactive agent, which may enhance tissue repair or limit the risk of sepsis, and/or any chemical additive (e.g., glycerol, 1-2 propandiol) which may modulate the mechanical properties (swelling rate in water, tensile strength and the like) of the film may be added during the preparation of the non-porous film formulation.

Bioactive Agents

In embodiments, at least one bioactive agent may be combined with one or more layers of the implant. In these embodiments, the implant may serve as a vehicle for delivery of the bioactive agent. The term "bioactive agent" as used herein, is used in its broadest sense and includes any substance or mixture of substances that have clinical use. Consequently, bioactive agents may or may not have pharmacological activity per se, e.g., a dye, or fragrance. In embodiments, a bioactive agent may be an agent that provides a therapeutic or prophylactic effect, a compound that effects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to any portion of the implant in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the implant and the surrounding tissues opposite the target tissue. In addition, anti-adhesive agents may be used to prevent adhesions from forming between the present implant and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the implant of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the implants of the present disclosure.

Other bioactive agents which may be included in the implant of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents that may be included in accordance with the present disclosure include, viruses and cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (e.g., IL-2, IL-3, IL-4, IL-6), interferons (e.g., 3-IFN, a-IFN, y-IFN), erythropoietin, nucleases, tumor necrosis factor, colony stimulating factors (e.g., GCSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Formation of Mono- and Multi-Layer Matrices

Figure 2:
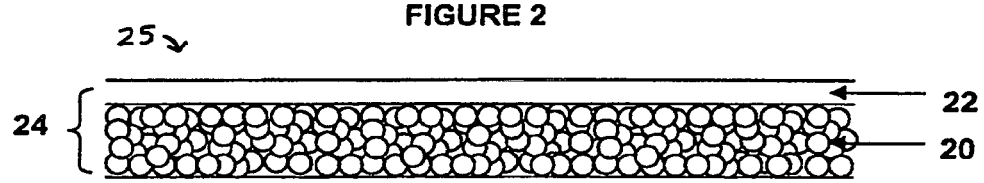
FIG. 2 is an illustration of a multi-layer implant including non-porous and porous layers in accordance with an embodiment of the present disclosure.

With reference to FIG. 1, implant 15 may be formed from a single porous chitosan layer 10, having a thickness 12. As shown in FIG. 2, implant 25 may be multi-layer, for example, a porous chitosan layer 20 may be coated with a non-porous layer 22 to form implant 25 having a thickness 24.

As stated above, although described herein with reference to a implant, the implant may be any type of scaffold, implant, and the like. When the implant described herein is multilayer, the implant may be formed using any method known to those skilled in the art capable of connecting a non-porous layer to a porous layer. It is envisioned that the non-porous layer and the porous layer may be adhered to one another using chemical bonding, surgical adhesives, surgical sealants, and surgical glues. In addition, the layers may be bound together using mechanic means such as pins, rods, screws, clips, sutures, staples, etc. Still further, the layers may naturally or through chemical or photoinitiation, interact and crosslink or provide covalent bonding between the layers.

In embodiments, a multilayer implant may be prepared by attaching the individual layers of materials together to form a multiple layer implant. The porous layer may be formed separate and apart from the non-porous layer. Alternatively, the porous and non-porous layers may be formed together. In embodiments, a two-layer implant may be prepared by first pouring a solution for a non-porous layer into an inert support or mold and distributing the solution for a non-porous layer evenly. This solution may be left to gel by the removal of solvent and cooling.

In embodiments, the mold or support is inert in that it does not react with the solution or the solutions constituents. The support may advantageously be made from a hydrophobic material such as, for example, PVC or polystyrene. However, this support may also consist of a strippable material, which may remain slightly adhesive and which may then be separated from the implant at the time of surgical use. The support may also consist of a film, for example dried collagen or a layer of collagenic material gel in a more advanced state of gellation, onto which the solution may be poured.

The density of the non-porous layer initially applied as a solution to the support may be from about 0.1 g solution/cm$^2$ to about 0.3 g solution/cm$^2$. This solution advantageously may be poured at a temperature from about 4° C. to about 30° C., and in embodiments from about 18° C. to about 25° C. Once applied to the support, the solution is allowed to partially gel. Partial gelling results from cooling of the solution, and not from drying of the solution. This solution may be left to gel and a porous layer previously prepared may be applied to the solution during gellation.

Application of the porous layer onto the partially gelled non-porous solution means placing the porous layer onto the gel, and optionally applying slight pressing. The pressing should be insufficient to cause any significant compaction of the porous layer.

The moment at which the porous layer is applied to the solution during gellation may depend upon the nature of the solution employed, the conditions under which the solution is maintained during gellation and the nature of the porous layer. Generally, the solution may be allowed to gel for a period of time prior to application of the porous layer, such that the gel is still soft and allows the porous layer to penetrate over a distance, which is advantageously from about 0.05 mm to about 2 mm and, in embodiments from about around 0.1 mm to about 0.5 mm. The appropriate moment for application of the porous layer for any given combination of materials/conditions may be determined empirically, for example by applying small samples of the porous layer to the gel at various times and evaluating the degree of penetration and adherence. Generally, when the solution, which is gelling, is at a temperature of between 4° C. and 30° C., the porous layer may be applied about 5 to about 30 minutes after the solution has been poured over the support holding it.

The composite layers may be left to dry or dried in order to obtain the final implant. When the solution used to form the non-porous film includes oxidized collagen, it may be polymerized while the material is drying. This drying may occur at a temperature of from about 4° C. to about 30° C. In embodiments, the drying may occur at a temperature from about 18° C. to about 25° C. The material may be dried in a jet of sterile air.

After drying, the implant may be separated from its support, packaged and sterilized using conventional techniques, e.g., irradiation with beta (electronic irradiation) or gamma (irradiation using radioactive cobalt) rays.

The present implants may be stable at ambient temperature and may remain stable for long enough periods of time to be handled at temperatures which may rise to about 37° C. to about 40° C. In accordance with the present disclosure, implants may be produced at any desired size or in large sheets later cut to sizes appropriate for the envisioned application.

The present implants may be implanted using open surgery or in a laparascopic procedure. When implanted laparoscopically, the present implants may be rolled with the porous side on the inside, before trocar insertion.

The following non-limiting example illustrates the preparation of implants in accordance with the present disclosure.

EXAMPLES

Porous chitosan layers useful as a mono-layer implant or as part of a multi-layer implant were prepared as follows:

Example 1

Chitosan Polymer Concentration 1%, Freeze-Dried at a pH of 5

A chitosan porous layer was prepared as follows: 1.21 g of chitosan (DA 2.5%) was solubilized in sterile water including a stoichiometric amount of acetic acid (0.437 g) over 6 hours until a 1% w/w solution was obtained. The pH of the chitosan solution was measured to be about 5.1. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

Figure 3A:
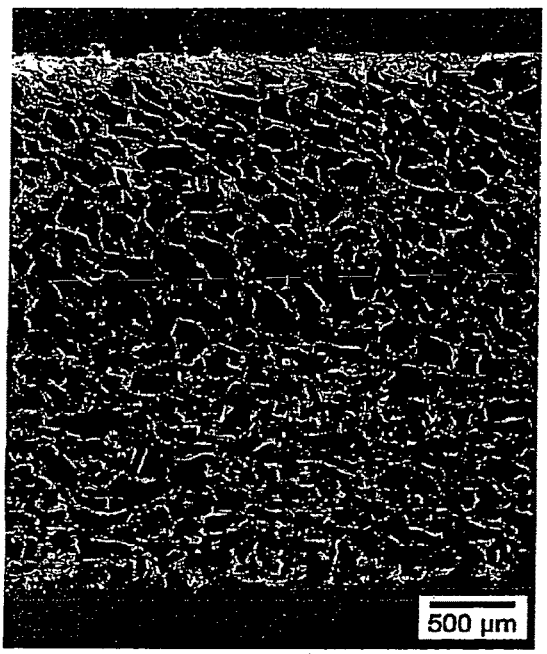
FIG. 3A is a scanning electron micrograph (SEM) image of a porous layer formed from a 1% concentration of a chitosan polymer solution.

FIG. 3A is an SEM image of the porous implant formed from a 1% chitosan solution which was freeze-dried at a pH of 5.

Example 2

Chitosan Polymer Concentration 0.8%, Freeze-Dried at a pH of 5

A chitosan porous layer was prepared as follows: 0.97 g of chitosan (DA 2.5%) was solubilized in sterile water containing a stoichiometric amount of acetic acid (0.350 g) for 6 hours until a solution at 0.8% w/w was obtained. At this stage, the pH of the chitosan solution was measured to be about 5.1. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

Figure 3B:
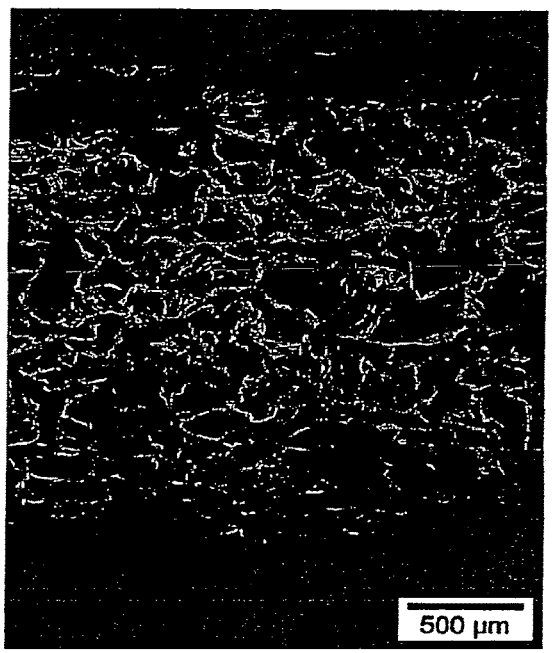
FIG. 3B is a scanning electron micrograph (SEM) image of a porous layer formed from a 0.8% concentration of a chitosan polymer solution.

FIG. 3B is an SEM image of the porous implant formed from a 0.8% chitosan solution which was freeze-dried at a pH of 5.

Example 3

Chitosan Polymer Concentration 1%, pH 3.5

A chitosan porous layer was prepared as follows: 1.24 g of chitosan (DA 2.5%) was solubilized in sterile water containing a stoichiometric amount of acetic acid (0.448 g) for 6 hours to obtain a 1.025% w/w solution. The pH of the chitosan solution was adjusted to 3.5 by adding 3 ml of acetic acid and the blend (a polymer concentration of 1%) was centrifuged. The final pH of the chitosan solution was 3.5. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

Figure 4A:
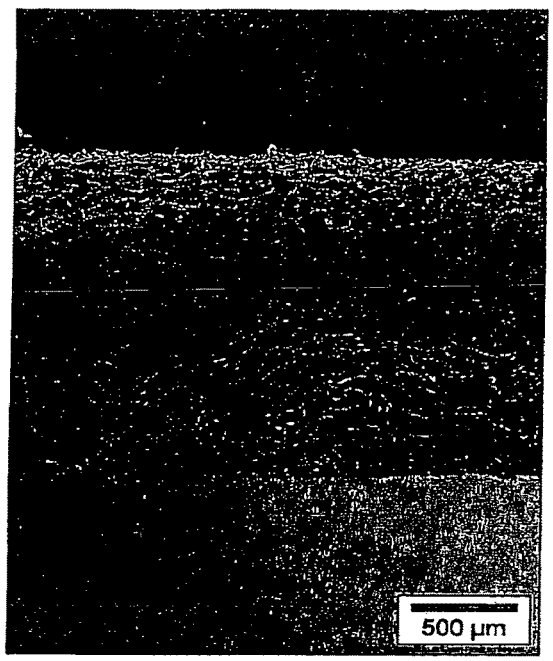
FIG. 4A is an SEM image of a porous layer formed from a 1% chitosan solution having the pH adjusted in accordance with an embodiment of the present disclosure.

FIG. 4A is an SEM image of the porous implant formed from a 1% chitosan solution which was freeze-dried at a pH of 3.5.

Example 4

Chitosan Polymer Concentration 0.8%, pH 3.5

A chitosan porous layer was prepared as follows: 0.99 g of chitosan (DA 2.5%) was solubilized in sterile water containing a stoichiometric amount of acetic acid (0.358 g) for 6 hours to obtain a 0.82% w/w solution. The pH of the solution was adjusted to 3.5 by adding 2.4 ml of acetic acid and the blend (new polymer concentration of 0.8%) was centrifuged. The final pH of the chitosan solution was 3.5. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

Figure 4B:
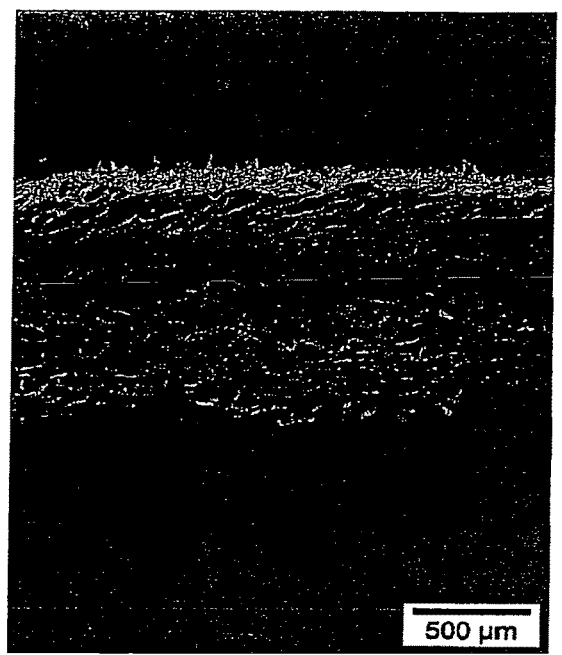
FIG. 4B is an SEM image of a porous layer formed from a 0.8% chitosan solution having the pH adjusted in accordance with an embodiment of the present disclosure.

FIG. 4B is an SEM image of the porous implant formed from a 0.8% chitosan solution which was freeze-dried at a pH of 3.5.

Example 5

Chitosan Polymer Concentration 1%, pH 3

A chitosan porous layer was prepared as follows: 1.32 g of chitosan (DA 2.5%) was solubilized in sterile water containing a stoichiometric amount of acetic acid (0.477 g) for 6 hours to obtain a 1.09% w/w solution. The pH of the solution was adjusted to 3 by adding 10.9 ml of acetic acid and the blend (new polymer concentration of 1%) was centrifuged. The final pH of the chitosan solution was 3.0. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

Figure 5:
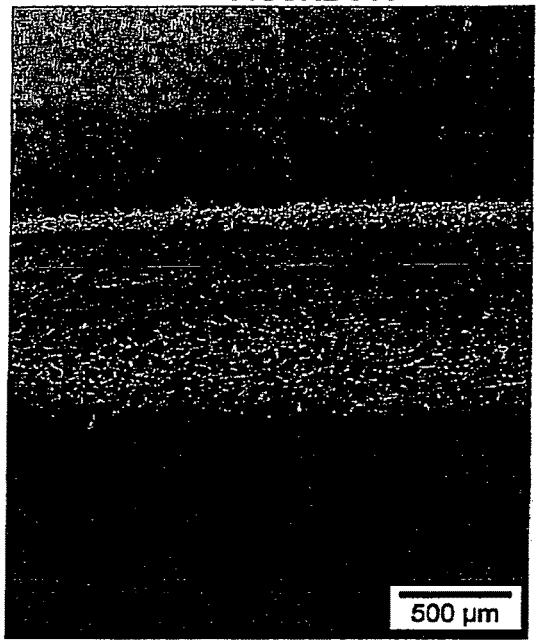
FIG. 5A is an SEM image of a porous layer formed from a 1% chitosan solution having the pH adjusted in accordance with an embodiment of the present disclosure.
FIG. 5B is an SEM image of a porous layer formed from a 0.8% chitosan solution having the pH adjusted in accordance with an embodiment of the present disclosure.
Figure 5:
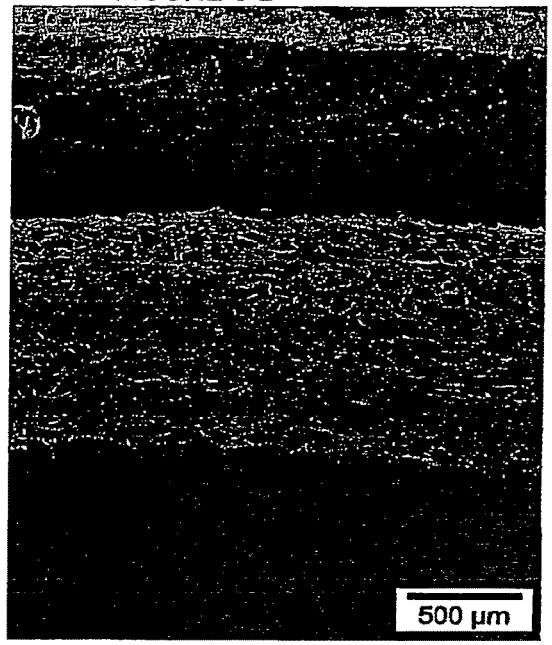

FIG. 5A is an SEM image of the porous implant formed from a 1% chitosan solution which was freeze-dried at a pH of 3.

Example 6

Chitosan Polymer Concentration 0.8%, pH 3

A chitosan porous layer was prepared as follows: 1.06 g of chitosan (DA 2.5%) was solubilized in sterile water containing a stoichiometric amount of acetic acid (0.382 g) for 6 hours to obtain a 0.87% w/w solution. The pH of the solution was adjusted to 3 by adding 8.7 ml of acetic acid and the blend (new polymer concentration of 0.8%) was centrifuged. The final pH of the chitosan solution was 3.0. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

FIG. 5B is an SEM image of the porous implant formed from a 0.8% chitosan solution which was freeze-dried at a pH of 3.

Example 7

Chitosan Polymer Concentration 0.8%, pH 1

A chitosan porous layer was prepared as follows: 1.06 g of chitosan (DA 2.5%) was solubilized in sterile water containing a stoichiometric amount of acetic acid (0.382 g) for 6 hours to obtain a 0.87% w/w solution. The pH of the solution was adjusted to 1 by adding 8.7 ml of acetic acid and hydrochloric acid, and the blend (new polymer concentration of 0.8%) was centrifuged. The final pH of the chitosan solution was 0.96. The aqueous chitosan solution was poured into a 12×17 cm mold and freeze-dried for 28 hours. The porous layer was then rinsed in an alkaline solution for 5 minutes, followed by being washed in sterile water until the pH of the porous layer was neutral. The neutral porous layer was then freeze-dried a second time to provide the porous layer for implantation.

Thickness of Resulting Matrices

Figure 6:
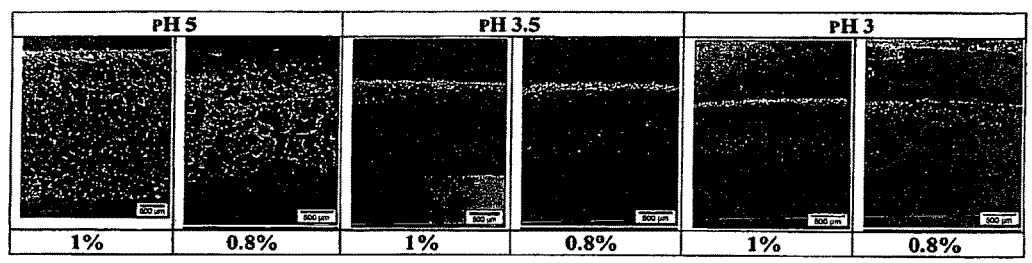
FIG. 6 is an SEM image of various porous chitosan layers described herein and in accordance with the present disclosure.

FIG. 6 includes SEM photos of each of the matrices resulting from solutions of examples 1-6 at 500 μm. The adjustment of the pH within the solution prior to freeze-drying modified the final thickness, after the neutralization step, of the resulting implant. As seen in FIG. 6, the lower the pH of the solution, the smaller the thickness of the resulting porous layer.

Tensile Strength and Suture Anchoring

Figure 7A:
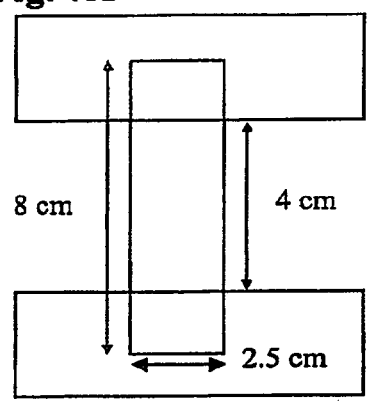
FIGS. 7A and 7B show the shapes used to determine tensile strength (FIG. 7A) and suture anchoring (FIG. 7B) of the implants.
Figure 7B:
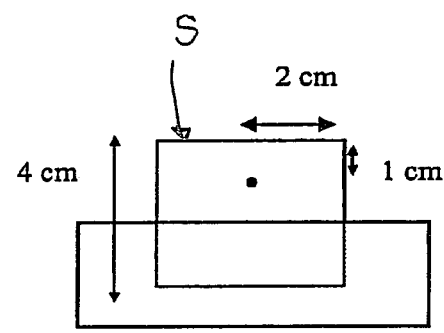

The evolution of the strength at break of the porous layer was evaluated against the initial pH of the solution. The samples of porous layer were cut into the desired shape and length as illustrated below:
The shape shown in FIG. 7A was used to test the tensile strength and the shape shown in FIG. 7B was used to determine suture anchoring. Prior to testing, the samples were hydrated in sterile water for 5 min.
Parameters of the mechanical testing:
  Tensile speed: 50 mm/min
  L(0) (for tensile test): 40 mm
  Cell force: 100 N, no 25943 (tensile test) and 25 N (suture test)
Table 3 contains the results for both the amount of elongation and force required to reach the breaking point of the implant. Table 4 demonstrates the amount of force and elongation of the implant prior to the suture detaching from the implant.

TABLE 3

| Implant | Force R (N) | Elongation R (%) | # Samples Tested |
|---|---|---|---|
| Example 1 | 3.64 ± 0.74 | 53.9 ± 7.5 | 8 |
| Example 2 | 2.41 ± 0.73 | 43.6 ± 6.4 | 8 |
| Example 3 | 10.21 ± 2.14 | 69.7 ± 11.8 | 8 |
| Example 4 | 13.07 ± 2.07 | 80.5 ± 4.0 | 5 |
| Example 5 | 18.17 ± 2.38 | 73.0 ± 6.2 | 8 |
| Example 6 | 11.64 ± 2.81 | 66.1 ± 8.6 | 8 |
| Example 7 | 9.19 ± 1.99 | 19.5 ± 3.1 | 8 |

TABLE 4

| Implant | Force R (N) | Elongation R (%) | # Samples Tested |
|---|---|---|---|
| Example 1 | 0.73 ± 0.07 | 14.1 ± 2.8 | 8 |
| Example 2 | 0.56 ± 0.08 | 13.8 ± 3.6 | 8 |
| Example 3 | 1.19 ± 0.11 | 16.1 ± 2.4 | 8 |
| Example 4 | 1.25 ± 0.27 | 14.7 ± 4.1 | 6 |
| Example 5 | 1.43 ± 0.24 | 14.1 ± 3.7 | 8 |
| Example 6 | 1.05 ± 0.26 | 13.9 ± 3.6 | 8 |
| Example 7 | 0.20 ± 0.09 | 5.0 ± 4.5 | 7 |

Figure 8:
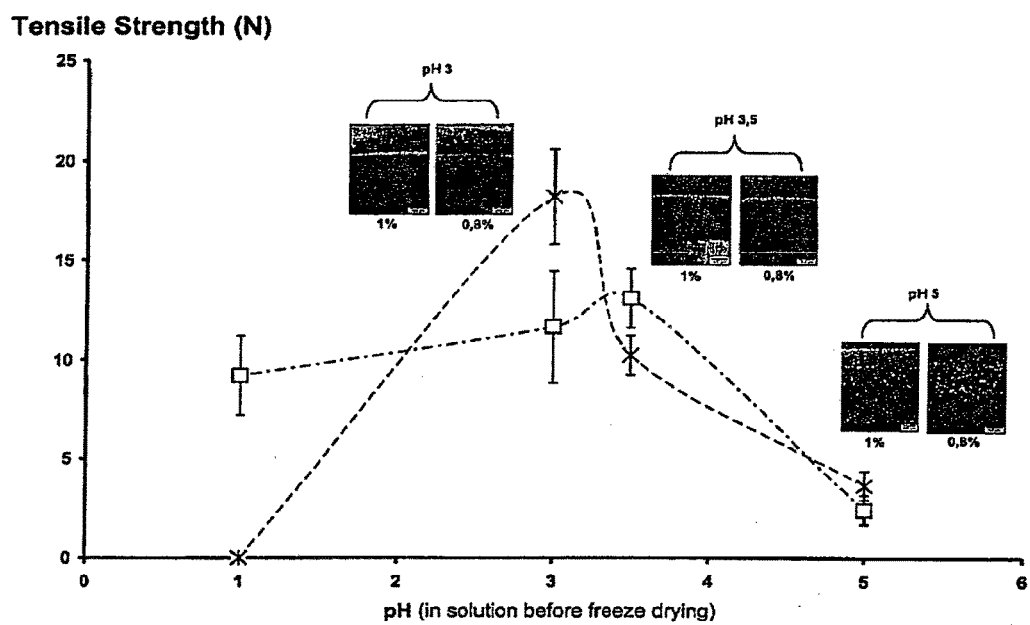
FIG. 8 is a graph of mechanical properties of implants in accordance with the present disclosure.

A comparison of the pH and the tensile strength of the implants are shown in FIG. 8. The pH of the chitosan solution prior to freeze-drying altered the mechanical properties of the porous layer. Irrespective of the polymer concentration, the pH creating the maximal strength at break is between 3 and 3.5. This tendency is slightly different between the two polymer concentrations tested. Therefore, density may not be the only the cause of the mechanical properties increased of the porous layer. Without wishing to be bound to any theory, it is believed that the variation of the pH may alter polymer chain orientation due to charge density variation along the polymer chain or deviation of the balance of the hydrophilic/hydrophobic interaction.

With respect to the polymer concentration, the greater the polymer concentration, the more polymer chain mobility is affected. The rearrangement of the polymer chain caused by pH variation required higher constraint resulting in a shift of the maximal strength at break at lower pH value as compared to the porous layer with 0.8% polymer concentration.

The effect of initial polymer concentration of the solution was apparent when the pH dropped below 2. The resulting porous layer showed a non-homogeneous structure especially at a polymer concentration of about 1.0% (w/w). The variation of the pH in the solution induces modifications within the structure of the final porous layer.

Example 8

Chitosan porous layers have been prepared according to the same manufacturing method as described in Example 1 but with the following varying parameters:
  1) Concentration of chitosan in the aqueous chitosan solution (Cp): two different concentrations were tested: Cp=0.8% by weight, and Cp=1% by weight
  2) Degree of acetylation of the chitosan used (DA): five different degrees of acetylation were tested: DA=2%, DA=10%, DA=20%, DA=30% and DA=40%
  3) Molecular weight of the chitosan used: four different molecular weights were tested: Mw=113000 g/mol, Mw=304000 g/mol, Mw=380500 g/mol and Mw=420000 g/mol.
  4) pH of the chitosan solution: four different pH were tested: pH=3, pH=3.5, pH=4 and pH=5.

The tensile strength, the elongation and the suture retention were tested for all chitosan porous layers thus prepared. The tests were performed on an extensometer Hounsfield ref H5KS equipped with a 100N cell. The tests were completed according to the following procedures:
1) Tensile strength and elongation: samples cut at 8×2.5 cm are prepared and hydrated. Each sample is maintained into pneumatic jaws and extension is performed at 50 mm/min till sample ruptures. Data are recorded with a 100N cell as shown on FIG. 7A. Maximum tensile strength to rupture is recorded, as well as maximum elongation to rupture.
2) Suture retention: the test consists in introducing a suturing yarn (Surgipro II 5-0) into a 4×4 cm sample S as shown on FIG. 7B. The bottom of the sample is maintained into jaws and the yarn is then pulled in the top direction at 50 mm/min till complete shearing of the sample. Maximum tensile strength of suture retention is recorded.

The results are shown in FIGS. 9-14.

FIG. 9 shows 3D diagrams representing the tensile strength (N) for the chitosan porous layers of the present example for a concentration in chitosan of 0.8%, respectively 1%, where the pH varies from 3 to 5 as described above, and where the DA varies from 2% to 40% as described above; in such cases, the molecular weight of the chitosan varies in function of the DA as follows: for DA equal to 2%, Mw is around 425000 g/mol; for DA equal to 10, 20 or 40%, Mw is around 513000 g/mol.

FIG. 10 shows 3D diagrams representing the tensile strength (N) for the chitosan porous layers of the present example for a concentration in chitosan of 0.8%, respectively 1%, and where the pH varies from 3 to 5 as described above and where the molecular weight (Mw) of the chitosan varies from 113000 to 420000 g/mol as described above. In such cases, the DA of the chitosans used is equal to 2%.

As appears from these Figures, the tensile strength of the chitosan porous layers of the present example increases when the pH of the chitosan solution decreases. In particular, the chitosan porous layers show good tensile strength when the pH of the chitosan solution is from about 3 to about 3.5. In particular, with reference to FIG. 9, the chitosan porous layers of the present example show good tensile strength when the pH of the chitosan solution is less than 4, preferably between 3 and 3.5, and when the degree of acetylation of the chitosan is less than 30%, preferably less than 20%. With reference to FIG. 10, the chitosan porous layers of the present example show good tensile strength when the pH of the chitosan solution is less than 4, preferably between 3 and 3.5, and when the molecular weight of the chitosan is equal or greater than 304000 g/mol.

FIG. 11 shows 3D diagrams representing the elongation (%) for the chitosan porous layers of the present example for a concentration in chitosan of 0.8%, respectively 1%, where the pH varies from 3 to 5 as described above, and where the DA varies from 2% to 40% as described above; in such cases, the molecular weight of the chitosan varies in function of the DA as follows: for. DA equal to 2%, Mw is around 425000 g/mol; for DA equal to 10, 20 or 40%, Mw is around 513000 g/mol.

FIG. 12 shows 3D diagrams representing the elongation (%) for the chitosan porous layers of the present example for a concentration in chitosan of 0.8%, respectively 1%, and where the pH varies from 3 to 5 as described above and where the molecular weight (Mw) of the chitosan varies from 113000 to 420000 g/mol as described above. In such cases, the DA of the chitosans used is equal to 2%.

As appears from these Figures, the chitosan porous layers of the present example show good elongation when the degree of acetylation of the chitosan is equal or greater than 10%, preferably equal or greater than 20%, especially when the concentration of the chitosan in the chitosan solution is 1% by weight.

FIG. 13 shows 3D diagrams representing the suture retention (N) for the chitosan porous layers of the present example for a concentration in chitosan of 0.8%, respectively 1%, where the pH varies from 3 to 5 as described above, and where the DA varies from 2% to 40% as described above; in such cases, the molecular weight of the chitosan varies in function of the DA as follows: for DA equal to 2%, Mw is around 425000 g/mol; for DA equal to 10, 20 or 40%, Mw is around 513000 g/mol.

FIG. 14 shows 3D diagrams representing the suture retention (N) for the chitosan porous layers of the present example for a concentration in chitosan of 0.8%, respectively 1%, and where the pH varies from 3 to 5 as described above and where the molecular weight (Mw) of the chitosan varies from 113000 to 420000 g/mol as described above. In such cases, the DA of the chitosans used is equal to 2%.

As appears from these Figures, the suture retention of the chitosan porous layers of the present example increases when the pH of the chitosan solution decreases. In particular, the chitosan porous layers of the present example show good suture retention when the pH of the chitosan solution is less than 4, preferably between 3 and 3.5, and when the molecular weight of the chitosan is equal or greater than 304000 g/mol.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. An implant for repair or substitution of biological tissue comprising:
    a chitosan porous layer including a tensile strength of about 4N or greater and an elongation percentage of about 40% or greater.
2. The implant of claim 1, wherein the chitosan porous layer includes chitosan having a degree of acetylation ranging from about 1% to about 40%.
3. The implant of claim 1, wherein the chitosan porous layer includes chitosan having a degree of acetylation less than about 30%.
4. The implant of claim 1, wherein the chitosan porous layer includes chitosan having a degree of acetylation less than about 20%.
5. The implant of claim 2, wherein the chitosan includes a mixture of chitosans having different degrees of acetylation.
6. The implant of claim 2, wherein the chitosan has a molecular weight equal to or greater than 304000 g/mol.
7. The implant of claim 1, wherein the tensile strength ranges from about 4N to about 20N.
8. The implant of claim 1, wherein the tensile strength ranges from about 10N to about 18N.
9. The implant of claim 1, wherein the elongation percentage is about 60% or greater.
10. The implant of claim 1, wherein the elongation percentage ranges from about 60% to about 85%.
11. The implant of claim 1, wherein the elongation percentage ranges from about 70% to about 80%.
12. The implant of claim 1, wherein the chitosan porous layer further includes a suture anchoring strength of at least about 0.8N.
13. The implant of claim 1, wherein the chitosan porous layer further includes a suture anchoring strength ranging from about 0.8N to about 1.5N.
14. The implant of claim 1, wherein the chitosan porous layer further includes a thickness ranging from about 0.1 mm to about 10 mm in a dry state.
15. The implant of claim 1, wherein the chitosan porous layer further includes a thickness ranging from about 0.1 mm to about 3 mm in a dry state.
16. The implant of claim 1, wherein the chitosan porous layer further includes a density ranging from about 0.25 mg/cm$^2$ of chitosan to about 20 mg/cm$^2$ of chitosan.
17. The implant of claim 1, wherein the biologic-al tissue is dura mater.
18. The implant of claim 1, wherein the chitosan porous layer further comprises at least one bioactive agent.
19. The implant of claim 1, further comprising a non-porous layer.
20. The implant of claim 19, wherein the non-porous layer comprises a collagen containing film.
21. The implant of claim 20, wherein the collagen containing film comprises a collagen selected from the group consisting of non-heated oxidized collagen, heated oxidized collagen, non-oxidized heated collagen and combinations thereof.
22. The implant of claim 20, wherein the collagen containing film further comprises at least one macromolecular hydrophilic additive.
23. The implant of claim 22, wherein the at least one macromolecular additive is selected from the group consisting of polyalkylene glycols, polysaccharides, oxidized polysaccharides, mucopolysaccharides, glycerin and combinations thereof.
24. The implant of claim 20, wherein the non-porous layer has a thickness of less than about 100 μm in a dry state.

* * * * *